(12) United States Patent
Adenusi et al.

(10) Patent No.: US 10,874,843 B2
(45) Date of Patent: Dec. 29, 2020

(54) MEDICAL DEVICE HYBRID POLYMERIC STRUCTURES AND COATINGS WITH IMPROVED LUBRICITY AND DURABILITY

(71) Applicant: Cardiac Pacemakers, Inc., St. Paul, MN (US)

(72) Inventors: Adegbola O. Adenusi, Burnsville, MN (US); James P. Rohl, Prescott, WI (US); David R. Wulfman, Minneapolis, MN (US); Joseph T. Delaney, Jr., Minneapolis, MN (US); Adeniyi Aremu, Brooklyn Park, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 284 days.

(21) Appl. No.: 15/972,611

(22) Filed: May 7, 2018

(65) Prior Publication Data

US 2018/0264248 A1 Sep. 20, 2018

Related U.S. Application Data

(62) Division of application No. 14/600,611, filed on Jan. 20, 2015, now Pat. No. 9,987,478.

(Continued)

(51) Int. Cl.
*A61F 2/06* (2013.01)
*A61F 2/86* (2013.01)
(Continued)

(52) U.S. Cl.
CPC ........... *A61M 39/08* (2013.01); *A61L 29/041* (2013.01); *A61L 29/06* (2013.01); *A61L 29/085* (2013.01);
(Continued)

(58) Field of Classification Search
CPC ............... A61F 2/06; A61F 2/07; A61L 31/10
(Continued)

(56) References Cited

U.S. PATENT DOCUMENTS 5,483,951 A 1/1996 Frassica et al.
6,610,035 B2 8/2003 Yang et al.
(Continued)

FOREIGN PATENT DOCUMENTS

CN 101128226 A 2/2008
CN 101939365 A 1/2011
(Continued)

OTHER PUBLICATIONS

International Preliminary Report on Patentability issued in PCT/US2015/012013, dated Aug. 4, 2016, 7 pages.
(Continued)

*Primary Examiner* — Ellen S Hock
(74) *Attorney, Agent, or Firm* — Faegre Drinker Biddle & Reath LLP

(57) ABSTRACT

A medical device made of a hybrid polymeric structure includes a tubular body including a first layer and a second layer. The first layer includes a fibrous matrix comprising a plurality of randomly oriented nanofibers made at least in part of a first polymeric material and pores formed between at least a portion of the nanofibers. The second layer is made at least in part of a second polymeric material. At least a portion of the second layer is disposed about and between the plurality of nanofibers such that at least a portion of the second polymeric material is embedded into at least a portion of the pores of the fibrous matrix.

18 Claims, 8 Drawing Sheets

Related U.S. Application Data

(60) Provisional application No. 61/929,886, filed on Jan. 21, 2014.

(51) Int. Cl.

| | | |
|---|---|---|
| *A61M 39/08* | (2006.01) | |
| *A61M 39/00* | (2006.01) | |
| *B32B 1/08* | (2006.01) | |
| *B32B 5/02* | (2006.01) | |
| *B32B 27/08* | (2006.01) | |
| *B32B 27/12* | (2006.01) | |
| *D01D 5/00* | (2006.01) | |
| *D01D 5/098* | (2006.01) | |
| *A61L 29/04* | (2006.01) | |
| *A61L 29/06* | (2006.01) | |
| *A61L 29/08* | (2006.01) | |
| *A61L 29/14* | (2006.01) | |
| *A61L 31/04* | (2006.01) | |
| *A61L 31/06* | (2006.01) | |
| *A61L 31/10* | (2006.01) | |
| *A61L 31/14* | (2006.01) | |
| *A61N 1/05* | (2006.01) | |

(52) U.S. Cl.
CPC ........... *A61L 29/145* (2013.01); *A61L 29/146* (2013.01); *A61L 31/048* (2013.01); *A61L 31/06* (2013.01); *A61L 31/10* (2013.01); *A61L 31/145* (2013.01); *A61L 31/146* (2013.01); *A61M 39/00* (2013.01); *A61N 1/056* (2013.01); *A61N 1/0541* (2013.01); *B32B 1/08* (2013.01); *B32B 5/02* (2013.01); *B32B 5/022* (2013.01); *B32B 27/08* (2013.01); *B32B 27/12* (2013.01); *D01D 5/0023* (2013.01); *D01D 5/0076* (2013.01); *D01D 5/0084* (2013.01); *D01D 5/0985* (2013.01); *B32B 2262/0238* (2013.01); *B32B 2535/00* (2013.01); *Y10T 428/1372* (2015.01)

(58) Field of Classification Search
USPC ......................................... 428/34.1; 623/1.44
See application file for complete search history.

(56) References Cited

U.S. PATENT DOCUMENTS

| | | | |
|---|---|---|---|
| 8,903,506 B2 | 12/2014 | Arnholt et al. | |
| 2001/0003796 A1 | 6/2001 | Yang et al. | |
| 2001/0027299 A1 | 10/2001 | Yang et al. | |
| 2009/0148489 A1 | 6/2009 | Cooper | |
| 2010/0198177 A1* | 8/2010 | Yahiaoui ................. | A61F 13/82 604/359 |
| 2011/0052787 A1 | 3/2011 | Hum et al. | |
| 2013/0041442 A1 | 2/2013 | Arnholt et al. | |
| 2013/0268062 A1* | 10/2013 | Puckett ................. | D01D 10/02 623/1.44 |
| 2015/0005869 A1* | 1/2015 | Soletti ................... | A61L 27/507 623/1.13 |

FOREIGN PATENT DOCUMENTS

| | | |
|---|---|---|
| CN | 102300537 A | 12/2011 |
| CN | 102596534 A | 7/2012 |
| JP | 2003500116 A | 1/2003 |
| JP | 2013500765 A | 1/2013 |
| WO | 1993015781 A1 | 8/1993 |
| WO | 1999055403 A1 | 11/1999 |
| WO | 2013078139 A1 | 5/2013 |
| WO | 2013151778 A1 | 10/2013 |

OTHER PUBLICATIONS

International Search Report and Written Opinion issued in PCT/US2015/012013, dated Apr. 20, 2015, 9 pages.

* cited by examiner

MEDICAL DEVICE HYBRID POLYMERIC STRUCTURES AND COATINGS WITH IMPROVED LUBRICITY AND DURABILITY

CROSS-REFERENCE TO RELATED APPLICATIONS

This application is a division of U.S. application Ser. No. 14/611,600, filed Jan. 20, 2015, which claims the benefit under 35 U.S.C. § 119(e) to U.S. Provisional Application 61/929,886, filed on Jan. 21, 2014, all of which are herein incorporated by reference in their entirety.

TECHNICAL FIELD

The present invention relates to medical devices and methods for manufacturing medical devices. More specifically, the invention relates to polymeric structures and coatings for medical devices and to methods for manufacturing polymeric structures and coatings for medical devices.

BACKGROUND

Polymeric structures used in the designing and manufacturing of medical devices may include two or more polymeric materials. The two or more polymeric materials within the polymeric structure may have different physical and/or chemical properties to help improve the mechanical properties of medical components and devices. Such polymeric structures have physical and/or chemical properties that are typically different from the original, polymeric materials.

A recognized challenge of creating polymeric structures is being able to combine two or more polymeric materials having different physical and/or chemical properties into a structure with adequate structural integrity. Furthermore, it can be a challenge obtaining suitable physical characteristics when combining two or more polymeric materials with different physical and/or chemical properties. A need for improving the polymeric structures and methods for manufacturing polymeric structures for medical devices continues to exist.

SUMMARY

Example 1 is a medical device made of a hybrid polymeric structure including a tubular body including a first layer and a second layer. The first layer includes a fibrous matrix comprising a plurality of randomly oriented nanofibers made at least in part of a first polymeric material and pores formed between at least a portion of the nanofibers. The second layer is made at least in part of a second polymeric material. At least a portion of the second layer is disposed about and between the plurality of nanofibers such that at least a portion of the second polymeric material is embedded into at least a portion of the pores of the fibrous matrix.

Example 2 is the medical device of Example 1, wherein the first layer includes the fibrous matrix made at least in part of the first polymeric material comprising poly(vinylidene fluoride-co-hexafluoropropylene) (PVDF HFP).

Example 3 is the medical device of either of Examples 1 or 2, wherein the fibrous matrix comprising the plurality of randomly oriented nanofibers, wherein a portion of the nanofibers are fused to one another.

Example 4 is the medical device of any of Examples 1-3, wherein the second layer is made at least in part of the second polymeric material comprising silicone.

Example 5 is the medical device of any of Examples 1-4, wherein the first layer further comprises a cross-linked hydrogel made at least in part of a third polymeric material disposed about and between the plurality of nanofibers.

Example 6 is the medical device of Example 5, wherein the cross-linked hydrogel is made at least in part of the third polymeric material comprising polyethylene glycol (PEG).

Example 7 is the medical device of either of Examples 5 or 6, further including a third layer disposed between the first layer and the second layer, the third layer including a portion of the fibrous matrix and not including the second polymeric material or the third polymeric material.

Example 8 is the medical device of any of Examples 5-7, wherein the first layer forms a first surface of the device and the second layer forms a second surface of the device.

Example 9 is the medical device of Example 8, wherein the first surface is an inner surface of the tubular body and the second surface is an outer surface of the tubular body.

Example 10 is a medical device including a tubular body including an outer surface, an inner surface, and a layer extending from the first surface to the second surface. The layer including a fibrous matrix, a first polymeric network and a second polymeric network. The fibrous matrix includes a plurality of randomly oriented nanofibers made at least in part of a first polymeric material and pores formed between at least a portion of the nanofibers. The first polymeric network is disposed within at least a portion of the pores. The first polymeric network is made at least in part of a second polymeric material. The second polymeric network is disposed within at least a portion of the pores. The second polymeric network is made a least in part of a third polymeric material.

Example 11 is the medical device of Example 10, wherein the first polymeric material includes poly(vinylidene fluoride-co-hexafluoropropylene).

Example 12 is the medical device of either of Examples 10 or 11, wherein the second polymeric material includes silicone.

Example 13 is the medical device of any of Examples 10-12, wherein the first polymeric material is hydrophobic and the third polymeric material is hydrophilic.

Example 14 is a medical device including a tubular body including an outer surface, an inner surface, and a layer extending from the outer surface to the inner surface. The layer includes a fibrous matrix including a plurality of randomly oriented nanofibers. The plurality of randomly oriented nanofibers a first plurality of nanofibers and a second plurality of nanofibers. The first plurality of nanofibers is made at least in part of a first polymeric material and the second plurality of nanofibers is made a least in part of a second polymeric material.

Example 15 is the medical device of Example 14, wherein the first plurality of nanofibers consists of the first polymeric material; and the second plurality of nanofibers consists of the second polymeric material.

Example 16 is the medical device of either of Examples 14 or 15, wherein the first polymeric material is hydrophilic and the second polymeric material is hydrophobic.

Example 17 is the medical device of any of Examples 14-16, wherein the first polymeric material is a thermoset material and the second polymeric material is a thermoplastic material, or the second polymeric material is a thermoset material and the first polymeric material is a thermoplastic material.

Example 18 is the medical device of any of Examples 14-17, wherein the first polymeric material is an electrically conductive material and the second polymeric material is an electrically non-conductive material, or the second polymeric material is an electrically conductive material and the first polymeric material is an electrically non-conductive material.

Example 19 is the medical device of Example 14, wherein the first polymeric material includes poly(styrene-isobutylene-styrene), polyisobutylene polyurethane, or a combination thereof; and the second polymeric material includes a polymer including polyethylene glycol.

Example 20 is the medical device of Example 14, wherein the first polymeric material includes poly(vinylidene fluoride-co-hexafluoropropylene) and the second polymeric material includes a polymer including polyethylene glycol.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
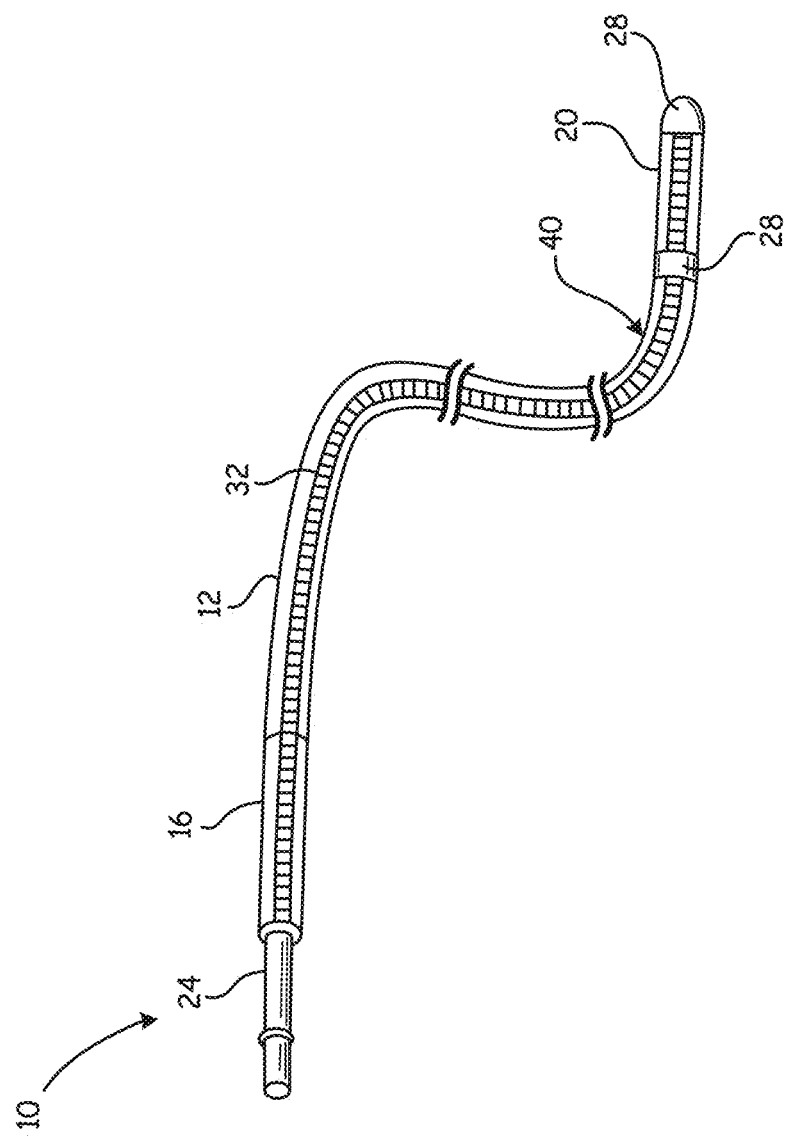
FIG. 1 is a schematic view of a medical electrical lead, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a partial cross-sectional view of a medical electrical lead 10, according to various embodiments of the present disclosure. According to some embodiments, the implantable electrical lead is configured for implantation within a patient's heart. According to some embodiments, the medical electrical lead is configured for implantation within a patient's neurovascular regions. In yet another embodiment, the lead can be a lead for a cochlear implant. Thus, the electrical lead can be used for a wide range of medical applications that deliver an electrical shock or pulse.

The medical electrical lead 10 includes an insulative, tubular body 12 extending from a proximal end 16 to a distal end 20. The proximal end 16 is configured to be operatively connected to a pulse generator (not shown) via a connector 24. At least one conductor 32 extends from the connector 24 at the proximal end 16 of the lead 10 to one or more electrodes 28 at the distal end 20 of the lead 10. The conductor 32 can be a coiled or cable conductor. According to some embodiments where multiple conductors 32 are employed, the lead 10 can include a combination of coiled and cable conductors 32. When a coiled conductor 32 is employed, according to some embodiments, the conductor 32 can have either a co-radial or a co-axial configuration.

The tubular body 12 is flexible, but substantially non-compressible along its length, and has a suitable cross-sectional shape. For example, tubular body 12 may have a generally circular cross-sectional shape. The tubular body 12 may be of a suitable size for implantation. For example, an outer diameter of the tubular body 12 may range from about 2 to about 15 French. The tubular body 12 may include a suitable bio-compatible, electrically insulative material. For example, in some embodiments, the tubular body 12 may include silicone or polyurethane. In some embodiments, the tubular body 12 may have a substantially uniform composition along its length. In other embodiments, the composition of the tubular body 12 may vary in any direction, including along the length and/or thickness.

The medical electrical lead 10 can be unipolar, bipolar, or multi-polar depending upon the type of therapy to be delivered. In some embodiments of the present disclosure employing multiple electrodes 28 and multiple conductors 32, each conductor 32 is adapted to be connected to an individual electrode 28 in a one-to-one manner allowing each electrode 28 to be individually addressable. Additionally, the tubular body 12 can include one or more lumens adapted to receive a guiding element such as a guidewire or a stylet for delivery of the lead 10 to a target location within a patient's heart.

The electrodes 28 can have any electrode 28 configuration as is known in the art. According to one embodiment of the present disclosure, at least one electrode 28 can be a ring or partial ring electrode 28. According to another embodiment, at least one electrode 28 is a shocking coil. According to yet another embodiment of the present disclosure, at least one electrode 28 includes an exposed electrode 28 portion and an insulated electrode 28 portion. In some embodiments, a combination of electrode 28 configurations can be used. The electrodes 28 can be coated with or formed from platinum, stainless steel, titanium, tantalum, palladium, MP35N, other similar conductive material, alloys of any of the foregoing including platinum-iridium alloys, and other combinations of the foregoing including clad metal layers or multiple metal materials.

According to various embodiments, the tubular body 12 can include one or more fixation members (not shown) for securing and stabilizing the tubular body 12 including the one or more electrodes 28 at a target site within a patient's body. The fixation member(s) can be active or passive. An exemplary active fixation member includes a screw-in fixation member. Examples of passive fixation members can include pre-formed distal portions of the tubular body 12 adapted to bear against vessel walls and/or expandable tines provided at the distal end 20 of the tubular body 12.

The lead 10 includes a hybrid polymeric structure 40 (also described as a hybrid polymeric coating) that is used to construct various parts of the insulative, tubular body 12. The hybrid polymeric structure 40 is composed of a combination of various polymers that includes at least two polymeric constituents having different physical and/or chemical properties.

Embodiments of the present disclosure include novel designs and methods for creating the hybrid polymeric structure 40 that combine two or more polymeric materials while maintaining suitable chemical and/or physical characteristics that are equivalent or substantially equivalent to at least one of the original precursor polymeric materials. In some embodiments, the hybrid polymeric structure 40 combines two or more polymeric materials to yield chemical and/or physical characteristics that would be unexpected from presently known polymeric structures comprising the same polymeric materials. For example, the hybrid polymeric structure 40 made of two polymers may have the stiffness characteristics of one of the precursor polymers, for example, the first polymeric material, and the lubricity characteristics of another precursor polymer, for example, the second polymeric material, according to embodiments of the present invention. A non-limiting example of the hybrid polymeric structure 40 includes a polymeric structure having a first polymeric material with higher stiffness than a second polymeric material. Another non-limiting example of the hybrid polymeric structure 40 includes the polymeric structure having the first polymeric material that exhibits hydrophobic characteristics and the second polymeric material that exhibits hydrophilic characteristics. Hydrophilicity (also termed as wettability) characterizes the ability of a surface to absorb water. In contrast, hydrophobicity characterizes an inability of a surface to absorb water, otherwise described as the ability of a surface to repel water.

The medical electrical lead 10 comprising the hybrid polymeric structure 40 can be used in various applications, according to various embodiments of the present disclosure. The tubular medical body 12 including a hybrid polymeric structure 40 can be used in various vascular medical applications that include, but are not limited to, cardiac implantable leads, balloon catheters, guide catheters and stents.

Figure 2:
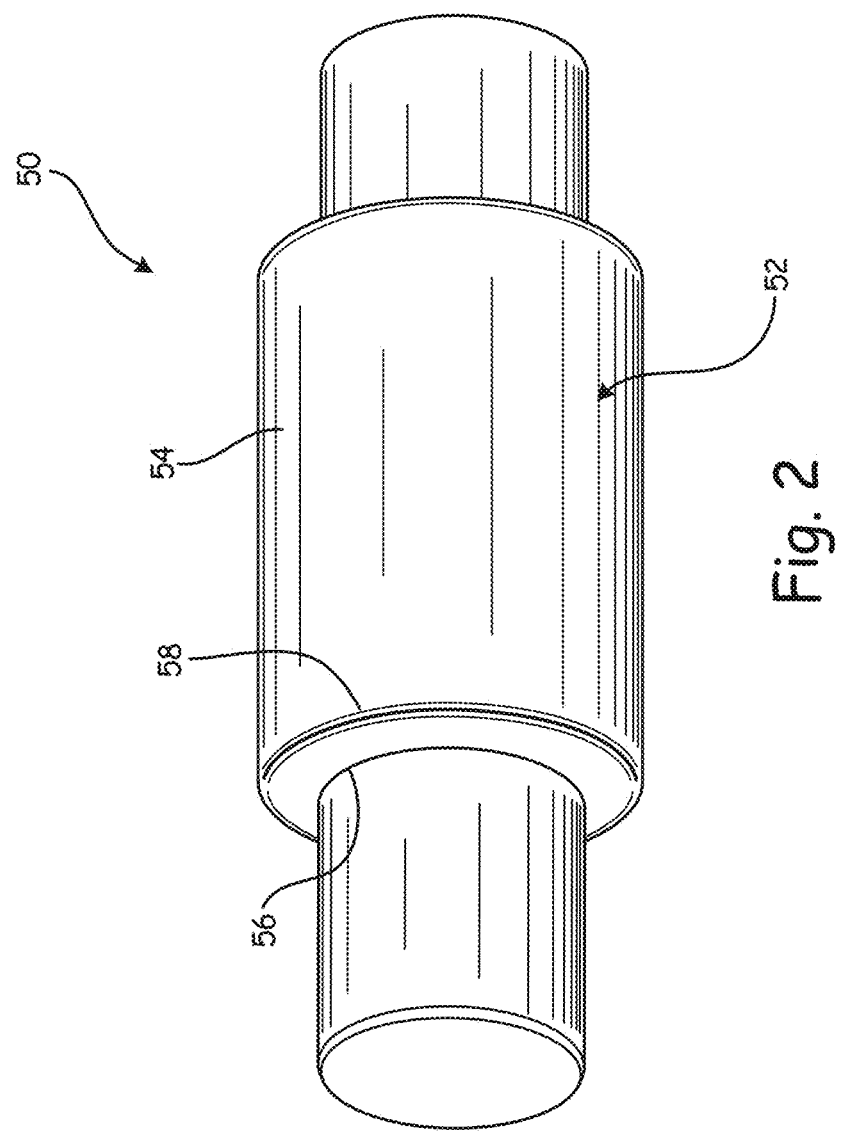
FIG. 2 is a schematic view of a tubular medical device having a hybrid polymeric structure, according to embodiments of the present invention.

FIG. 2 is a schematic view of an illustrative but non-limiting example of a medical device 50 with a tubular body 52, for example, the tubular body 12 of the medical electrical lead 10 (FIG. 1). As shown, the tubular body 52 is formed of a hybrid polymeric structure 54, according to embodiments of the present invention. In some embodiments, the tubular body 52 of the medical device 50 includes a first surface 56, for example, an inner surface, and a second surface 58, for example an outer surface. The medical device 50 optionally has a tubular body 52 that is flexible, but non-compressible along its length, and has a suitable cross-sectional shape. For example, the tubular body 52 of a medical device 50 may have a generally circular cross-sectional shape. As discussed herein, the hybrid polymeric structure 54 can provide several advantages to various medical devices 50. For example, the hybrid polymeric structure 54 produces the medical device 50 providing certain dissimilar, but preferable characteristics to a single tubular body 52, according to embodiments of the present disclosure.

In some embodiments, the hybrid polymeric structure 54 can be used to form the tubular medical device 50 with a first polymeric material that provides increased lubricity to the inner luminal surface of the tubular medical device 50 and a second polymeric material that provides the desired stiffness characteristics to the body 52 of the device 50. In other embodiments, the hybrid polymeric structure 54 includes the first polymeric material to provide increased durability to the exterior surfaces of the medical device 50 and the second polymeric material to provide a suitable stiffness characteristic in the body 52 of the device 50. In some embodiments, the hybrid polymeric structure 54 can produce the medical device 50 with exterior and/or luminal surfaces composed of the first polymeric material to promote increased anti-inflammatory, anti-microbial, biocompatible effects in a patient's body, and a portion of the body 52 of the device 50 with the second polymeric material to provide suitable mechanical characteristics.

The tubular body 52 of the medical device, for example, a medical lead, can be of a suitable size for implantation within a patient's vascular system, according to embodiments of the present disclosure. The outer diameter of a tubular body 52 of the medical device may range from about 0.04 inches (1.0 mm), or about 3 French, to about 0.39 inches (10 mm), or about 30 French, for example. In other embodiments, the outer diameter of a tubular body 52 of the medical device may range from about 0.026 inches (0.667 mm), or about 2 French, to about 0.197 inches (5.00 mm), or about 15 French, for example. Suitable outer diameter sizes for the medical device may also range from about 0.019 inches (0.500 mm) to about 0.039 inches (1.00 mm), from about 0.059 inches (1.50 mm) to about 0.138 inches (3.50 mm), 0.079 inches (2.00 mm) to about 0.118 inches (3.00 mm), 0.10 inches (2.5 mm) to about 1.0 inches (25 mm), 0.5 inches (13 mm) to about 1.0 inches (25 mm), 0.7 inches (17 mm) to about 1.0 inches (25 mm), for example. The wall thickness of the tubular body 52 of the medical device may range from about 0.002 inches (0.051 mm) to about 0.005 inches (0.127 mm), for example.

The tubular medical device 50 including the hybrid polymeric structure 54 may be used in various medical applications, according to embodiments of the present invention. For example, the hybrid polymeric structure 54 can be incorporated into tubular medical devices 50 for use in applications such as intubation tubes, feeding tubes, and drainage tubes. For intubation applications, the hybrid polymeric structure 54 can be used in intubation tubes that target the tracheal, nasal, oral, or larangeal mask passageways, for example, Sengstaken-Blakemore tubes or orotracheal tubes, according to some embodiments. For feeding tube applications, the hybrid polymeric structure 54 can be used in nasogastric, nasojejunal, gastric, and ostomy ports procedures, for example, a gastric sleeve, an endotracheal tube, an endoscope tube, or an endoscope introducer, according to some embodiments. For drainage tube applications, the hybrid polymeric structure 54 can be used in gastric tubes, pulmonary chest tubes, post-surgical tubes or introducers, and post-infection tubes or introducers, according to some embodiments.

In some embodiments, the tubular body 52 of the medical tube is of a suitable size for short-term diagnostic procedures within a patient's fluid passageway. The tubular body 52, for example, the tracheostomy tube, may have an outer diameter ranging from about 0.35 inches (9 mm), or about 27 French, to about 0.51 inches (13 mm), or about 29 French, for example. The outer diameter of the tubular body 52 may be about 0.78 inches (2 cm), or about 60 French, for example. In some embodiments, the inner diameter of the tubular body 52 may range from about 0.2 inches (6 mm) to about 0.4 inches (9 mm), for example. The wall thickness of the medical tube may be about 0.10 inches (2.54 mm).

Figure 3:
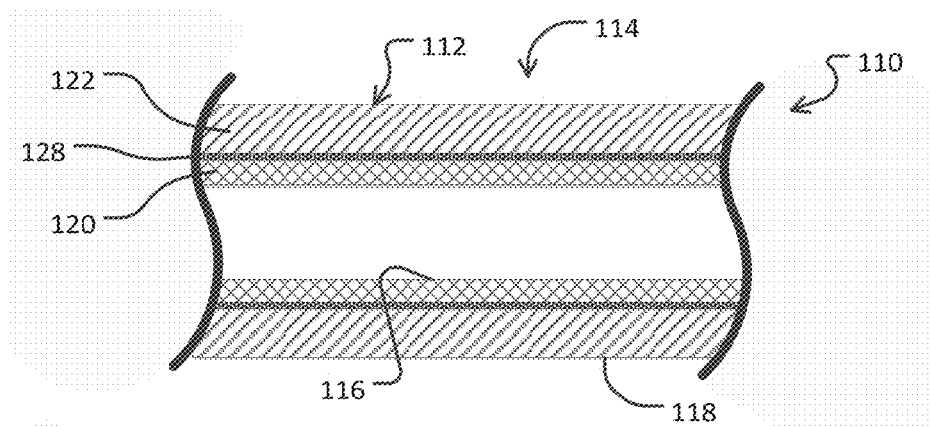
FIG. 3 is a schematic longitudinal cross-section of an alternative embodiment of the implantable medical device of FIG. 2, according to embodiments of the present invention.

FIG. 3 is a schematic longitudinal cross-section of an alternative embodiment of an implantable medical device 110 having a tubular body 112, according to embodiments of the present invention. As shown, the tubular body 112 includes a first layer 120 and a second layer 122. In some embodiments, the first layer 120 is an inner layer having a first surface 116 forming an interior surface of the tubular body 112 and the second layer 122 is an outer layer forming an exterior surface of the tubular body 112.

At least a portion of the tubular body 112 of the medical device 110 is constructed of the hybrid polymeric structure 114, according to embodiments of the present invention. In some embodiments, the entire tubular body 112 of the medical device 110 is constructed of the hybrid polymeric structure 114. In some embodiments, the tubular body 112 is made in part of a hybrid polymeric structure 114 having multiple portions, wherein each portion has a different composition of polymeric materials. In some embodiments, the hybrid polymeric structure 114 includes two or more polymeric materials that are non-uniformly disposed as separate layers within the structure. As such, the composition of one layer of the structure is optionally different from the composition of another layer of the same structure.

As shown in FIG. 3, the different portions of the hybrid polymeric structure 114 are represented as radial layers within the tubular body 112, according to embodiments of the present invention. The tubular body 112 optionally includes one or multiple layers of polymeric material between the first and second surfaces 116, 118. For example, in some embodiments, the hybrid polymeric structure 114 includes one, two, three, four or five layers.

In some embodiments, the first layer 120 is composed of a first polymeric material and the second layer 122 is composed of a second polymeric material. In some embodiments, the first and second layers 120, 122 form the hybrid polymeric structure 114 because the polymeric materials of the first and second layers are structurally and/or chemically distinct. For example, the first and second layers 120, 122, optionally form the tubular body 112 having the hybrid polymeric structure 114 because the first polymeric material of the first layer 120 is structurally and/or chemically distinct from the second polymeric material of the second layer 122. In some embodiments, the tubular body 112 is composed of two or more layers, wherein one layer is composed of one or more polymers, a particular composition of polymers and/or a particular physical form of the one or more polymers.

The hybrid polymeric structure 114 optionally includes various physical forms of polymeric materials. In some embodiments, the hybrid polymeric structure 114 includes a fibrous matrix and a polymeric network (also described as a surrounding polymer matrix, impregnating polymer material). In some embodiments, the hybrid polymeric structure 114 includes the fibrous matrix, the polymeric network and a non-fibrous polymeric layer.

The fibrous matrix is a porous polymeric structure constructed of a plurality of discrete fibers, according to embodiments of the present invention. The fibrous matrix includes pores, also described as spaces or voids, formed between a given fiber and one or more neighboring fibers, as desired. In some embodiments, the pores of the fibrous matrix are embedded with another polymeric material. In some embodiments, the embedded polymer within the fibrous matrix forms a polymeric network. In some embodiments, the polymeric network is a polymeric structure formed by one or more polymeric materials that have become embedded in the pores of the fibrous matrix.

Together, the fibrous matrix of one material and the polymeric network of another material optionally form an embedded fibrous matrix (also described as an impregnated or integrated fibrous matrix). In some embodiments, the embedded fibrous matrix is composed of polymeric materials of the first and second layers, wherein the polymeric material of the second layer 122 is embedded into the polymeric material of the first layer 120. Described differently, the embedded fibrous matrix optionally includes a structure having the fibrous matrix made of the first polymeric material and the polymeric network made of the second polymeric material. A non-limiting example of the embedded fibrous matrix includes a portion of the first layer 120, e.g. the fibrous matrix made of the first polymeric material, embedded with a portion of the second layer 122, e.g. the polymer network made of the second polymeric material.

The non-fibrous polymeric layer can be polymeric material that does not embed into the fibrous matrix. In some embodiments, the non-fibrous polymeric layer is optionally disposed adjacent a layer that includes the fibrous matrix. In some embodiments, the first layer (e.g. inner layer) or the second layer (e.g. outer layer) is composed of the non-fibrous polymeric layer. In some embodiments, the hybrid polymeric structure includes the non-fibrous polymeric layer and the embedded polymer both made from the same polymeric material.

In some embodiments, the first layer 120 is composed of the first polymeric material in the form of the fibrous matrix and the second layer 122 is composed of the second polymeric material in the form of the non-fibrous polymeric layer. Alternatively, in other embodiments, the first layer 120 is composed of the first polymeric material in the form of the non-fibrous polymeric material and the second layer 122 is composed of the second polymeric material in the form of the fibrous matrix. In each of these types of embodiments, the first and second layers 120, 122 form the tubular body 112 having the hybrid polymeric structure 114 because the first polymeric material of the first layer 120 is structurally and/or chemically distinct from the second polymeric material of the second layer 122. Generally, a transition between the first and the second layer 120, 122 forms yet another layer, in some embodiments.

As shown in FIG. 3, the tubular body 112 of the medical device 110 includes a third layer 128, an intermediate layer, between the first and second layers 120, 122. In some embodiments, a transition from the first layer 120 to the second layer 122 optionally occurs at the third layer 128. In some embodiments, the third layer 128 includes at least a portion of the first layer 120, for example, the inner layer, and at least a portion of the second layer, for example, the outer layer 122. In some embodiments, at least a portion of one layer (e.g. the first layer) embeds, or integrates, into at least a portion of an adjacent layer (e.g. the second layer). Alternatively, in some embodiments, at least a portion of the one layer (e.g. the first layer) is optionally embedded by at least a portion of an adjacent layer (e.g. the second layer).

In some embodiments, the third layer 128 is in the form of the embedded fibrous matrix. For example, in some embodiments, the third layer includes at least a portion of the second layer 122 that is embedded into the first layer 120. In other embodiments, the third layer includes a portion of the first layer 120 that is embedded in the second layer 122. A non-limiting example of the third layer 128 includes the embedded fibrous matrix resulting from the combination of the first and the second layers 120, 122, wherein the first layer 120 comprises the fibrous matrix made of the first polymeric material and the second layer 122 comprises the polymeric network made of the second polymeric material. Furthermore, a non-limiting example of the hybrid polymeric structure 114 includes the first layer 120 composed of the fibrous matrix 124 of the first polymeric material, the second layer 122 being composed of a non-fibrous polymeric layer of the second polymeric material, and the third layer 128 composed of the polymeric network made of the second polymeric material that is embedded within the fibrous matrix made of the first polymeric material.

Figure 4:
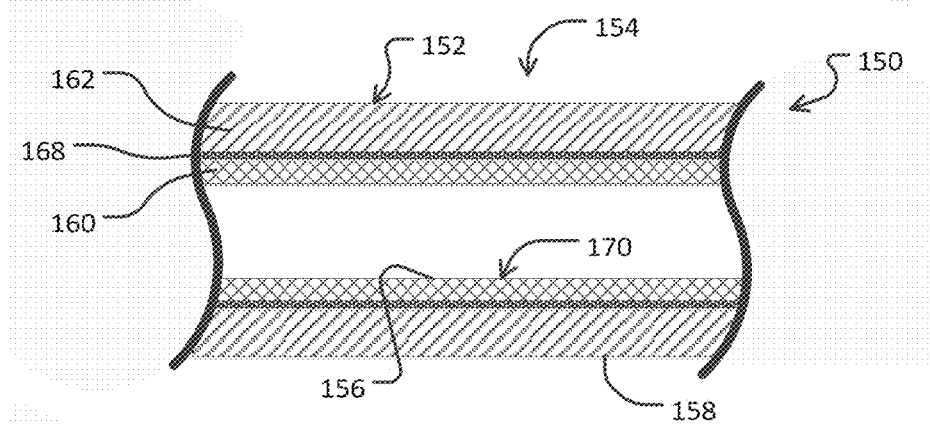
FIG. 4 is a schematic longitudinal cross-section of an alternative embodiment of the implantable medical device of FIG. 2, according to embodiments of the present invention.

FIG. 4 is a schematic longitudinal cross-section of an alternative embodiment of an implantable medical device 150 having a tubular body 152, according to embodiments of the present invention. As shown, the tubular body 152 includes a first layer 160 having a first surface 156 and a second layer 162 having a second surface 158. For example, in some embodiments, the first layer 160 is an inner layer, the second layer 162 is an outer layer, the first surface 156 is an inner surface of the tubular body 152 and the second surface 158 is an outer surface of the tubular body 152. In some embodiments, the first layer 160 can be composed of a first and second polymeric material in the form of a cross-linked hydrophilic polymer coating 170. The first polymeric material can be in the form of a fibrous matrix and the second polymeric material can be a hydrogel in the form of a polymeric network embedded in the fibrous matrix.

As shown in FIG. 4, in some embodiments, the hybrid polymeric structure 154 includes the first layer 160 composed of the first and second polymeric material in the form of the cross-linked hydrophilic polymer coating and the second layer 162 composed of a third polymeric material in the form of the non-fibrous polymeric layer. In some embodiments, a third layer 168 (e.g. an intermediate layer) is formed between the first and second layers 160, 162 that includes the embedded fibrous matrix resulting from a combination of portions of the first and the second layers 160, 162. In some embodiments, the third layer 168 includes a portion of the first layer 160 comprising the cross-linked hydrophilic polymer coating 170 made of the first and second polymeric materials and a portion of the second layer 162 comprising the non-fibrous polymeric layer made of the third polymeric material. In other words, the third layer 168 is the embedded fibrous matrix optionally made of the fibrous matrix composed of the first polymeric material and embedded polymers composed of both the second and third polymeric materials. In other embodiments, the third layer 168 includes a portion of the first layer 160 comprising the (non-embedded) fibrous matrix made of the first polymeric material and a portion of the second layer 162 comprising the non-fibrous polymeric layer made of the third polymeric material. In other words, the third layer 168 is an embedded fibrous matrix optionally made of the fibrous matrix composed of the first polymeric material and the embedded polymer composed of the third polymeric material only.

In some embodiments, the hybrid polymeric structure 154 includes the first layer 160 composed of the first and second polymeric material in the form of the cross-linked hydrophilic polymer coating and the second layer 162 composed of the first polymeric material and a third polymeric material in the form of the embedded fibrous matrix, wherein the first polymeric material is in the form of a fibrous matrix, the second polymeric material is in the form of a first polymeric network (e.g. a hydrogel) embedded in the fibrous matrix, and the third polymeric material is in the form of a second polymeric network embedded in the fibrous matrix. In some embodiments, the hybrid polymeric structure 154 optionally includes the third layer 168 (e.g. intermediate layer) between the first and second layers 160, 162, wherein the third layer 168 includes the fibrous matrix made of the first polymeric material with no embedded polymer.

Figure 5:
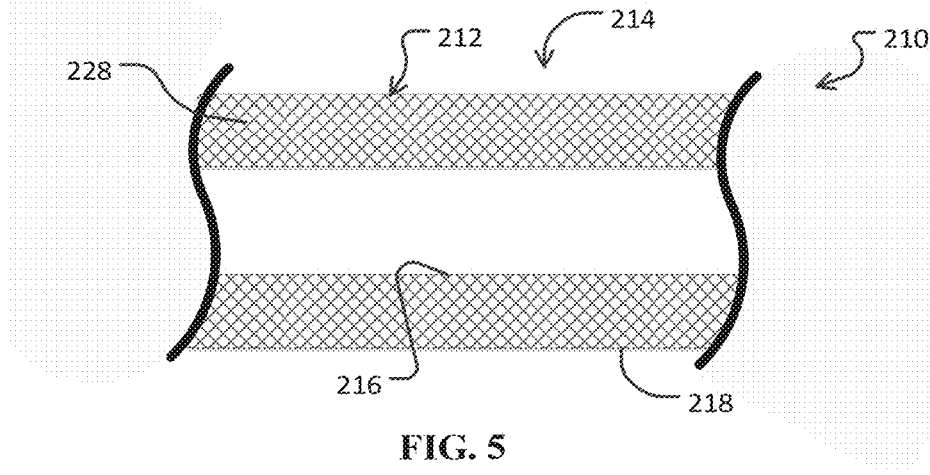
FIG. 5 is a schematic longitudinal cross-section of an alternative embodiment of the implantable medical device of FIG. 2, according to embodiments of the present invention.

FIG. 5 is a schematic longitudinal cross-section of another embodiment of the implantable medical device 210 made of a hybrid polymeric structure 214, according to embodiments of the present invention. As shown, the embodiment of the medical device 210 and the previously discussed embodiments of the medical device 110, 10 are optionally substantially similar, and thus various features of the embodiment of the medical device 210 are described in association with the previously discussed medical device 110, 10.

In FIG. 5, the medical device 210 has a tubular body 212 including a first surface 216, e.g. an inner surface, and a second surface 218, e.g. an outer surface. As shown, the hybrid polymeric structure 214 has a layer 228, extending from the first surface 216 to the second surface 218, that includes first and second polymeric materials. In some embodiments, the layer 228 of the hybrid polymeric structure 214 includes two polymeric materials, wherein the first polymeric material has different chemical and/or physical characteristics than the second polymeric material. In some embodiments, the hybrid polymeric structure 214 includes a fibrous matrix that includes fibers of two or more polymeric materials. For example, the fibrous matrix optionally includes a first plurality of fibers made of the first polymeric material and a second plurality of fibers made of the second polymeric material.

The layer 228 of the hybrid polymeric structure 214 optionally includes the fibrous matrix made of the first polymeric material and a polymeric network made of the second polymeric material, according to embodiments of the present invention. In some embodiments, the fibrous matrix includes a smaller or a larger portion of the first polymeric material relative to the second polymeric material.

In some embodiments, the layer 228 of the hybrid polymeric structure 214 optionally includes the fibrous matrix and multiple polymeric networks. In some embodiments, each polymeric network is made of a different polymeric material. For example, the layer 228 of the hybrid polymeric structure 214 optionally includes the fibrous matrix made of the first polymeric material, the first polymeric network made of the second polymeric material, and the second polymeric network made of a third polymeric material. In some embodiments, the hybrid polymeric structure 214 includes a larger portion of the first polymeric material relative to the second polymeric network. In other embodiments, the hybrid polymeric structure 214 includes a smaller portion of the first polymeric material relative to the second polymeric network. Described differently, the fibrous matrix includes a smaller or a larger portion of the second polymeric material relative to the third polymeric material, wherein the first polymeric network is made of the second polymeric material, and the second polymeric network is made of the third polymeric material.

Figure 6:
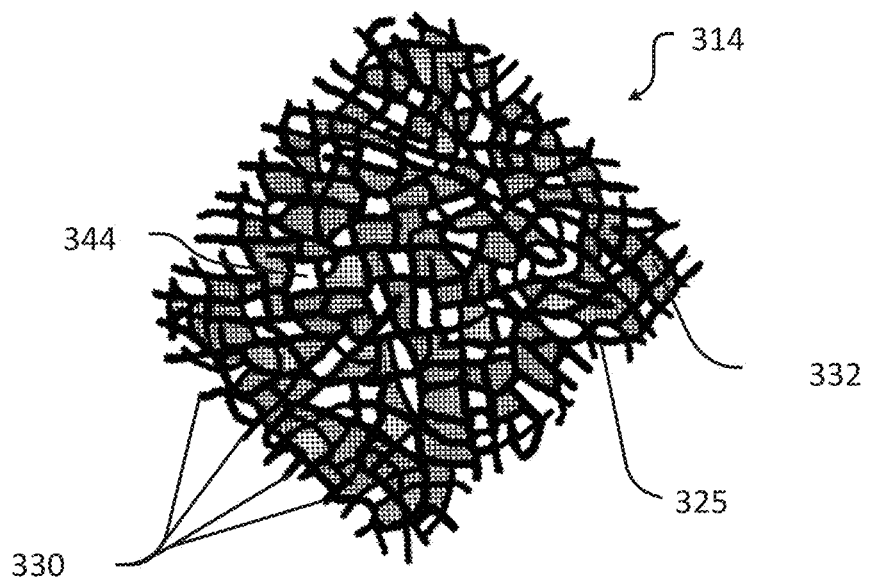
FIG. 6 is a schematic illustration of the hybrid polymeric structure, according to embodiments of the present invention.

FIG. 6 shows an illustrative, but non-limiting example of a polymer layer made of a hybrid polymeric structure 314 including a fibrous matrix 325 and an embedded polymer 332. As shown, the fibrous matrix is composed of a plurality of discrete fibers 330 made of a first polymeric material and the embedded polymer of a second polymeric material.

The fibrous matrix 325 includes fibers 330 that overlap with one another to create pores 344, also described as spaces or voids, between a given fiber 330 and one or more neighboring fibers 330, according to embodiments of the present invention. The pores 344 may be formed between neighboring fibers 330 in any direction, including along the length, width and thickness of the fibrous matrix 325. The pores 344 of the fibrous matrix 325 may vary in shape and size. The pores 344 may be interconnected with other pores 344 within the matrix 325. In some embodiments, the pores 344 create a continuous porous network within the matrix 325. In some embodiments, the pores 344 create a continuous porous network from a first surface 116, 156, e.g. the inner surface, of the fibrous matrix 325 to an opposite layer surface, for example, a surface of the intermediate layer 128, 168 or the second surface 118, 158, e.g. the outer surface, of the fibrous matrix 325 (see FIGS. 3-5). In certain embodiments, the plurality of pores 344 created by the fibers 330 may extend through the matrix 325 in all three spatial directions (i.e., in the x, y, z directions).

In some embodiments, as shown in FIG. 6, the fibrous matrix 325 may be a nonwoven matrix. For example, the fibrous matrix 325 may comprise a plurality of randomly aligned fibers 330. In other embodiments, the fibrous matrix 325 may be a woven matrix in which the fibers 330 are oriented in a repeating pattern or configuration. As further described herein, the fibrous matrix 325 may be formed by various methods that include but are not limited to, for example, blow melting, electrospinning and force spinning.

The fibrous matrix 325 may be of any suitable thickness that yields suitable physical and/or chemical characteristics for the tubular medical device having the hybrid polymeric structure. For example, the fibrous matrix 325 may have a thickness in the range of about 0.0001 inches (2.54 microns) to about 0.001 inches (25.4 microns). Suitable fibrous matrix thicknesses also include about 0.001 inches (25.4 microns) to 0.01 inches (254 microns), or about 0.001 inches (25.4 microns) to 0.005 inches (1.27 mm), about 0.01 inches (254 microns) to 0.015 inches (381 microns), or about 0.002 inches (508 microns) to 0.004 inches (1.0 mm), or about 0.003 inches (0.8 mm) to 0.005 inches (1.27 mm), for example. In another example, the fibrous matrix 325 may have a thickness in the range of about 500 nanometer (nm) to about 300 microns. A suitable fibrous matrix 325 thickness range also includes the range of about 15 microns to 250 microns, for example. In other examples, the average thickness of the fibrous matrix 325 may be about 0.0035 inches (90 microns).

The fibers 330 of the fibrous matrix 325 may have diameters in the range of about 100 nanometer (nm) to 10,000 nm, for example. The fiber diameter size may be about 100 nm to 3,000 nm, for example. Suitable fiber diameter sizes also include about 40 nm to 2,000 nm, about 100 nm to 1,500 nm or about 100 nm to 1,000 nm, for example. In still further examples, the fiber diameter may be 100 nm to 800 nm, or 100 nm to 400 nm. In other examples, the average fiber diameter may be 400 nm to 10 microns or 800 nm to 10 microns.

As mentioned previously herein, the fibers 330 within the fibrous matrix 325 can create pores 344 of varying sizes within the matrix 325. Fiber configuration and diameter may affect average pore size and range of the pore size of the pores 344 within the matrix 325. For example, a nonwoven fibrous matrix 325 having fibers 330 with a diameter ranging between 0.2-1.0 microns may produce a matrix 325 having a pore size range between 1 nm and 0.5 microns.

Suitable materials for the fibers 330 of the fibrous matrix 325 include both conductive and non-conductive polymer materials, according to embodiments of the present invention. In some embodiments, the fibers 330 of the fibrous matrix 325 include both thermoplastic and thermoset materials. In some embodiments, the fibers 330 of the fibrous matrix 325 include both hydrophilic and hydrophobic materials. In some embodiments, the fibers 330 of the fibrous matrix 325 are formed from a fluoropolymer material. Suitable fluoropolymer materials for the fibers 330 may include polytetrafluoroethylene (PTFE), polyvinylidene fluoride (PVDF) (e.g. Kynar™ and Solef™) and poly(vinylidene fluoride-co-hexafluoropropene) (PVDF-HFP). Suitable polymers for fibers 330 are formed from urethane-based polymers include but are not limited to, for example, polyurethanes, polyether-based polyurethanes (e.g. Tecothane), polycarbonate polyurethanes (e.g. Bionate and/or Chronoflex) and/or combinations thereof. Other examples of suitable polymer materials for the fibers 330 include, and are not limited to, polycarbonate, polyether, polyester, polyamide, nylon 6, nylon 12, polyetherimide and/or combinations thereof. Suitable polymers for fibers 330 are formed from olefin based polymers, for example, polyethylene glycol (PEG). In some embodiments, the fibers 330 of the fibrous matrix 325 are formed from a block polymer, for example, poly(styrene-isobutylene-styrene) (SIBS) tri-block polymer and polyisobutylene polyurethane (PIB-PUR) and/or combinations thereof.

As shown in FIG. 6, the hybrid polymeric structure 314 also includes the embedded polymer 332, according to embodiments of the present invention. The embedded polymer 332 is a polymeric network formed from the second polymeric material located between the fibers 330 of the fibrous matrix 325. In some embodiments, the embedded polymer 332 forms a polymeric network, wherein the second polymeric material is located in between the fibers 330, i.e. within the pores 344, of the fibrous matrix 325. In some embodiments, the fibrous matrix 325 of the first polymeric material and the polymeric network of the second polymeric material together to form the hybrid polymeric structure 314 because the first polymeric material is structurally and/or chemically distinct from the second polymeric material.

In some embodiments, the embedded polymer 332 is disposed within the pores 344 of the fibrous matrix 325 such that at least a portion of the surfaces of individual fibers 330 within the matrix 325 are covered by the second polymeric material. In certain embodiments, the embedded polymer is disposed within the pores 344 to cover a substantial portion or a majority portion of the fibers 330 within the matrix 325. In some embodiments, the embedded polymer is disposed within at least a portion of the pores 344 of the matrix 325. The embedded polymer is optionally disposed within the pores 344 to cover only a portion of the fibers 330 within the matrix 325 at a particular location, for example, at an intermediate layer where the fibrous matrix couples to another polymeric material (FIGS. 3 and 4).

Suitable materials for the embedded polymer and/or the non-fibrous polymeric material include both conductive and non-conductive polymer materials, according to embodiments of the present invention. In some embodiments, the embedded polymer and/or the non-fibrous polymeric material include both hydrophilic and hydrophobic materials. In some embodiments, suitable materials for the embedded polymer and/or the non-fibrous polymeric material include various thermoplastic polymers and thermoset polymers. In some embodiments, the embedded polymer and/or the non-fibrous polymeric material may comprise multiple thermoplastic polymers, thermoset polymers, and/or combinations thereof. In some embodiments, suitable materials for the embedded polymer and/or the non-fibrous polymeric material include polymers that are suitable to various application processes that include, but are not limited to, for example, dip coating, spraying, electro spraying, electrospinning, injection molding, extruding and/or combinations thereof.

Exemplary thermoset polymers include, but are not limited to, polyurethanes, silicone polymers, phenolic polymers, amino polymers, epoxy polymers, and/or combinations thereof.

Exemplary thermoplastic polymers include, but are not limited to, polyurethanes, polyether block amides (e.g. Pebax™), polyvinyl chloride (PVC), polyamides, polyesters, polyacrylates, polystyrene (PS), silicones, latex rubber, poly-(styrene-ethylene-butylenestyrene) (SEBS), poly-(styrene-b-isoprene-b-styrene) (SIS), poly-(styrene-b-ethylene-co-propylene-b-styrene) (SEPS), poly(styrene-b-isoprene/butadiene-b-styrene) (SEEPS), copolymers of ethylene and propylene, LDPE, LLDPE, VLDPE, polypropylene (PP), polyethylene (PE), and copolymers of ethylene and propylene, metallocene polymerized polyolefins, ethylene methacrylate (EMA), ethylene ethyl acrylate (EEA), Ethvlene-n-butyl acrylate copolymer (EnBA), ethylene-butene, ethylene-octene, ethylene vinyl acetate (EVA), ethylene vinyl alcohol (EVOH) and maleic anhydride grafted ethylene vinyl acetate (EVA g-MAH); fluorinated polyolefins (such as polytetrafluoroethylene, copolymers of tetrafluoroethylene and hexafloropropylene (FEP), perfluoroalkoxy polymer resin (PFA), polychlorotrifluoroethylene (pCTFE), copolymers of ethylene and chlorotrifluoroethylene (pECTFE), and copolymers of ethylene and tetrafluoroethylene (PETFE)) and/or combinations thereof.

Figure 7:
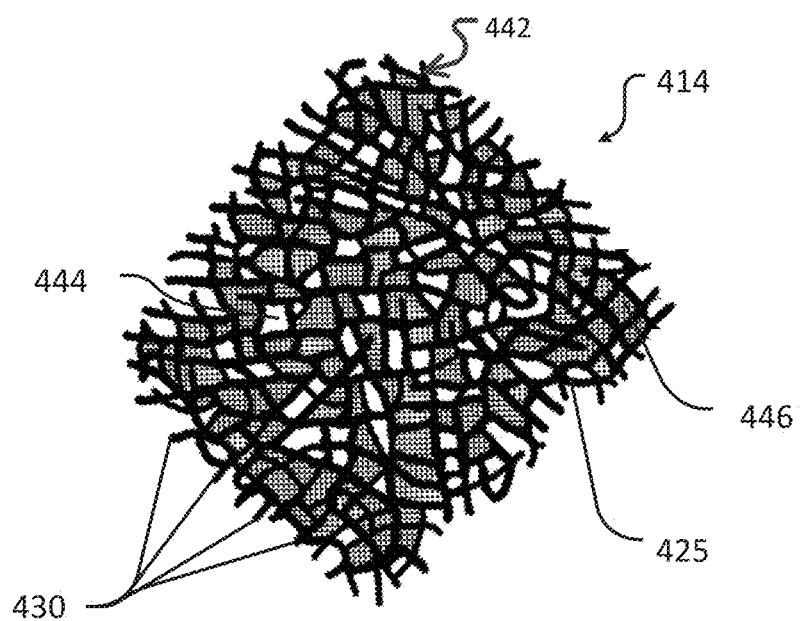
FIG. 7 is a schematic illustration of an alternative embodiment of the hybrid polymeric structure, according to embodiments of the present invention.

FIG. 7 shows an illustrative, but non-limiting example of a hybrid polymeric structure 414 including a fibrous matrix 425 and an embedded polymer. In some embodiments, the embedded polymer is a hydrophilic hydrogel 446, wherein the fibrous matrix 425 and the hydrophilic hydrogel 446 together optionally form a cross-linked hydrophilic polymer coating 442. The hydrophilic hydrogel 446 and the previously discussed embodiments of the embedded polymer are similarly disposed within the pores of the fibrous matrix, in some embodiments. Various features of the hydrophilic hydrogel 446 are therefore described in association with the previously discussed embedded polymer 432, in some embodiments. As shown, the fibrous matrix is composed of a plurality of discrete fibers 430 made of a first polymeric material and the hydrophilic hydrogel 446 of a second polymeric material.

The hydrogel is a network of hydrophilic polymer chains located between the fibers 430 of the fibrous matrix 425, according to some embodiments. Cross-linked hydrophilic polymer coatings 442 are generally described in U.S. Application No. 61/856,959, filed Jul. 22, 2013 entitled Improved Lubricious, Biocompatible Hydrophilic Thermoset Coating Using Interpenetrating Hydrogel Networks, which is incorporated herein by reference in its entirety.

In some embodiments, when the hydrogel 446 is disposed within the pores 444, the hydrogel 446 may either completely fill or partially fill the pores 444 of the fibrous matrix 425. For example, the hydrogel 446 may fill at least one-third of the total volume of the pores 444 within the fibrous matrix 425. In another example, the hydrogel 446 may fill at least three-fourths of the total volume of the pores 444 within the fibrous matrix 425. In some embodiments, the hydrophilic hydrogel 446 may interpenetrate the pores 444 of the fibrous matrix 425 and create an interconnected hydrogel network throughout the interior of the fibrous matrix 425. In some embodiments, the hydrogel network may extend from a first surface of the fibrous matrix 425 to a second and opposite surface of the fibrous matrix 425 by interpenetrating, filling, or being disposed within the pores of the matrix 425. In some embodiments, the hydrogel network partially interpenetrates the pores 444 of the matrix 425, such that only a portion of the fibrous matrix forms the fibrous matrix 425. The hydrogel 446 serves to increase the hydrophilicity of the fibrous matrix 425, which in turn, may provide the medical device with increased sensing and pacing properties and/or lubricity properties.

The cross-linked hydrophilic polymer coating may be of any suitable thickness that provides suitable physical and/or chemical characteristics to the medical device composed of the hybrid polymeric structure. For example, the cross-linked hydrophilic polymer coating may have a thickness in the range of about 500 nanometer (nm) to 300 microns. A suitable coating thickness range also includes the range of about 15 microns to 250 microns, for example. In other examples, the average coating thickness of the cross-linked hydrophilic polymer coating may be about 90 microns (or 0.0035 inches).

Suitable materials for the hydrogel 446 include materials that increase the hydrophilicity of the cross-linked hydrophilic polymer coating 442 as compared to the fibrous matrix 425. In some embodiments, the hydrogel 446 may comprise one or more thermoset polymers. In other embodiments, the hydrogel 446 may comprise one or more thermoplastic polymers. In yet other embodiments, the hydrogel may comprise a combination of thermoplastic and thermoset polymers. In some embodiments, the hydrogel 446 comprises a polyethylene glycol (PEG) or a PEG derivative, for example, PEG-dimethacrylate, UV-curable PEG, PEG diacrylate, polyethylene glycol-neopentyl glycol diacrylate methyl acrylate (PEG-NPDGA), PEG-Bioslide™, PEG-Z-Glide™ chitosan-PEG, thiol-PEG, maleimide-PEG, amino-PEG, azide-PEG, and carboxyl-PEG. Examples of other hydrophilic materials include, but are not limited to, polyvinylpyrrolidone (PVP), polyvinyl acetate (PVA), glycosaminoglycans (e.g. heparin), poly [N-(2-hydroxypropyl) methacrylamide] (PHPMA), poly(vinyl pyrrolidone), polyethylene/oligoethylene, polyHEMA, polytetraglyme, hyalorunic acid, chitosan, and any derivatives thereof.

The average number molecular weight of the hydrogel polymer constituent may affect the physical integrity of the cross-linked hydrophilic polymer coating 442. For example, a hydrogel 446 comprising a low number molecular weight PEG may yield a more ductile cross-linked hydrophilic polymer coating 442 than one that uses a hydrogel 446 comprising a high number molecular weight PEG. In some embodiments, a hydrogel 446 comprises a polymer having a low number molecular weight. For example, a low number molecular weight (MN) PEG may have a number molecular weight range from about 400 g/mol to 1,000 g/mol, or about 400 g/mol to 5,000 g/mol. In other embodiments, a hydrogel 446 comprises a polymer having a high number molecular weight. For example, a high number molecular weight PEG may have a number molecular weight range from about 5,000 g/mol to 1,200,000 g/mol. In some examples, a high number molecular weight PEG may have a molecular weight range from about 550 g/mol to 1,000 g/mol, about 5,000 g/mol to 30,000 g/mol, about 5,000 g/mol to 300,000 g/mol, about 5,000 g/mol to 900,000 g/mol, about 600,000 g/mol to 900,000 g/mol, or about 5,000 g/mol to 1,000,000 g/mol.

In some embodiments, the hydrogel 446 may be incorporated into the fibrous matrix 425 by cross-linking a hydrogel solution that also includes a curing initiator. Cross-linking may be achieved using a wide variety of free radical initiators, such as a thermal initiator or a photoinitiator. A thermal initiator is a chemical compound that decomposes and produces free radicals when subjected to heat. A photointiator is a chemical compound that produces free radicals when exposed to UV light. The curing initiator may be added to the hydrogel solution prior to the hydrogel 446 being applied to the fibrous matrix 50. Exemplary methods of curing include, but are not limited to, the use of heat, UV, argon plasma treatment and/or combinations thereof.

In some embodiments, peroxide may be used as the free radical initiator. Peroxide free radical initiators are thermal initiators that may be prepared from alcohols, ketones, and acids. Such peroxides may also be further stabilized or derivativized through the formation of ethers, acetals, and esters. Examples of commonly commercially available peroxides include, but are not limited to, benzoyl peroxide, dibenzoyl peroxide, 2-butanone peroxide, t-butylperacetate, t-butylperoxide, 2,5-di(t-butylperoxy)-2,5-dimethyl-3-hexyne, dicumyl peroxide, 2,4-pentanedione peroxide, 1,1-bis(tert-butylperoxy)cyclohexane, lauroyl peroxide, t-butylperoxy 2-ethylhexyl carbonate, 1,1'-azobis(cyclohexanecarbonitrile), 1,1-bis(tert-butylperoxy)-3,3,5-trimethylcyclohexane, 1,1-bis(tert-butylperoxy)cyclohexane, 2,2'-azobis(2-methylpropionamidine) dihydrochloride, 2,2'-azobis(2-methylpropionitrile), 2,2'-azobis(2-methylpropionitrile), 2,5-bis(tert-butylperoxy)-2,5-dimethylhexane, 2,5-di(tert-butylperoxy)-2,5-dimethyl-3-hexyne, 2-butanone peroxide, 4,4'-azobis(4-cyanovaleric acid), azobisisobutyronitrile, cumene hydroperoxide, dicumyl peroxide, lauryl peroxide, tert-butyl hydroperoxide, tert-butyl peroxide, tert-butyl peroxybenzoate, and tert-butylperoxy 2-ethylhexyl carbonate.

In some embodiments, a redox initiator may be used to produce free radicals. Different metal salts can produce radicals when reacting with peroxides, for example, the salts of the following cations: $Cr^{2+}$, $V^{2+}$, $Ti^{3+}$, $Co^{2+}$, $Fe^{2+}$, and $Cu^+$. In some embodiments, inorganic peroxides may be used, such as ammonium persulfate, potassium persulfate, or sodium persulfate, for example.

In other embodiments, an azo initiator may be used as the free radical initiator to cross-link hydrophilic hydrogel 446. Azo initiators are thermal initiators derived from diasene and have the functional group R—N+N—R', where R and R' are either an aryl or alkyl group. Examples of azo free radical initiators include, but are not limited to, 2,2'-azobisisobutyronitrile (AIBN), 1,1'-azobis(cyclohaxanecarbonitrile), and 4,4-azobis(4-cyanovaleric acid).

In some embodiments, a photoinitiator may be used as the free radical initiator. In some embodiments, the free radical photoinitiators may include acetophenone-based derivatives and benzyl-based derivatives. Examples of free radical photoinitiators include, but are not limited to, 4-(2-hydroxyethoxy)phenyl-(2-hydroxy-2-propyl)ketone (such as Irgacure® 2959, available from BASF), benzil, benzoin, benzophenone, 2,2-dimethoxy-2-phenylacetophenone, 1-hydroxycyclohexylphenyl ketone, 2,2-diethoxyacetophenone, 2,2-dimethoxy-2-phenylacetophenone, 2-hydroxy-2-methylpropiophenone, 2-hydroxy-4'-(2-hydroxyethoxy)-2-methylpropiophenone, 2-methyl-4'-(methylthio)-2-morpholinopropiophenone, 2-methylbenzophenone, 2-tert-butylanthraquinone, 3,4-dimethylbenzophenone, 3'-hydroxyacetophenone, 3-methylbenzophenone, 4-(diethylamino)benzophenone, 4-(dimethylamino)benzophenone, 4,4'-bis(diethylamino)benzophenone, 4,4'-bis[2-(1-propenyl)phenoxy]benzophenone, 4,4'-dihydroxybenzophenone, 4,4'-dimethoxybenzoin, 4,4'-dimethylbenzil, 4'-ethoxyacetophenone, 4'-hydroxyacetophenone, 4'-phenoxyacetophenone, 4'-tert-butyl-2',6'-dimethylacetophenone, 4-benzoylbiphenyl, 4-hydroxybenzophenone, 4-methylbenzophenone, 9,10-phenanthrenequinone, benzoin ethyl ether, benzoin methyl ether, benzophenone, benzophenone-3,3',4,4'-tetracarboxylic dianhydride, camphorquinone, diphenyl(2,4,6-trimethylbenzoyl)phosphine oxide, methyl benzoylformate, Michler's ketone, phenylbis(2,4,6-trimethylbenzoyl)phosphine oxide, and sodium anthraquinone-2-sulfonate.

In some embodiments, glutaraldehyde, formaldehyde, formalin, and related compounds can be used as crosslinking agents for polyfunctional alcohols, for example, acetals, and for amines, for example, imines or enamines.

Hydrogels 446 may be applied to the fibrous matrix 425 to create a cross-linked hydrophilic polymer coating 442 that is more hydrophilic than the fibrous matrix 425. The hydrophilicity of a material composed of a fibrous matrix 425 may therefore be enhanced by disposing the hydrogel 446 within the pores 444 of the fibrous matrix 425. In some embodiments, the hydrogel 446 is disposed within the pores 444 of a fibrous matrix 425 having fibers 430 that exhibit a lower hydrophilicity than the hydrogel 446. For example, a PEG hydrogel 446 may be disposed within the pores 444 of a SIBS fibrous matrix 425 to produce the cross-linked hydrophilic polymer coating 442 that is more hydrophilic than the matrix 425 because the PEG hydrogel 446 is a more hydrophilic material than the SIBS material. In other embodiments, the hydrogel 446 is disposed within the pores 444 of a fibrous matrix 425 having fibers 430 that exhibit hydrophobicity.

Methods of Creating Hybrid Polymeric Structures and Coatings

The hybrid polymeric structure 314, 214, 114, 14 may be formed using various methods and processes discussed herein. In some embodiments, the non-limiting examples of various methods and processes are provided hereinafter.

The fibrous matrix of the hybrid polymeric structure may be constructed using various processes, for example, electrospinning, melt blowing, force spinning, and/or combinations thereof. The processes discussed herein or other similar processes may be used to construct a fibrous matrix. In certain embodiments, the fiber matrix may be formed partially or completely with fibers using modified electrospinning, melt-blowing and force spinning techniques. Methods for forming the fibrous matrix are generally described in U.S. application Ser. No. 13/571,553, filed Aug. 10, 2012, entitled METHOD FOR COATING DEVICES USING ELECTROSPINNING AND MELT BLOWING, which is incorporated herein by reference in its entirety. In some embodiments, the fibrous matrix may be constructed into a tubular shape by using the processes discussed herein by forming the fibrous matrix about a mandrel, or other similar shaped tools.

In electrospinning, an electric field may be used to draw a polymer solution or melt from a capillary source. In some embodiments, the capillary source may be a syringe. The polymer solution or melt is drawn to a grounded collector. A high voltage power supply may be used to power the process. The element to be coated, such as a substrate, may be placed on the collector to be coated. Upon drying, the electrospun material may form a thin polymeric web. In some embodiments, the fiber sizes may be controlled by adjusting the relative concentration of polymer in the polymer solution or melt.

In melt-blowing, an apparatus is configured to accommodate a polymer melt. The polymer melt passes through an orifice and is carried through the orifice via streams of hot air that pass through the apparatus. As the polymer melt exits the orifice, it is met with streams of heated air that helps elongate the polymer melt. As a result, the polymer melt forms fibers that impinge onto a collector. An element to be coated, such as a substrate, may simply be placed on or in front of the collector.

In force spinning, also called centrifugal force spinning, a polymeric material is atomized by centrifugal forces and sprayed onto a targeted element. Force spinning involves a spinneret, also described as a rotary sprayer. Polymeric solutions or melts are placed into the spinneret and are drawn from a spinneret orifice by centrifugal forces. The centrifugal forces overcome the surface tension of the solution or melt, producing a polymer jet that can be sprayed onto the targeted element. The polymer jet exiting from the spinneret stretches, dries and solidifies to produce nanofibers on the targeted element.

The hybrid polymeric structure optionally includes the non-fibrous polymeric layer. In some embodiments, the non-fibrous polymeric layer is formed using various processes, for example, by dip coating, spraying, electro spraying, electrospinning, injection molding, extruding, and/or combinations thereof. In some embodiments, the hybrid polymeric structure is created by forming the non-fibrous polymeric layer prior to forming the fibrous matrix. In other embodiments, the hybrid polymeric structure is created by forming the non-fibrous polymeric layer after the fibrous matrix is formed. In some embodiments, the hybrid polymeric structure is created by forming the non-fibrous polymeric layer and the fibrous matrix simultaneously. In some embodiments, at least a portion of the non-fibrous polymeric layer will embed into the fibrous matrix using the processes herein.

In some embodiments, the hybrid polymeric structure includes the polymeric network and the non-fibrous polymeric layer having the same polymeric material, for example, the first polymeric material. The non-fibrous layer and the polymeric network are optionally formed by adding the first polymeric material in the pores of the fibrous matrix beyond a pore saturation point. Pore saturation occurs when nearly all of the accessible pores of the fibrous matrix have become filled with a polymer, for example, the first polymeric material. Once the pore saturation point has been achieved, any additional amounts of a polymeric material, e.g. the first polymeric material, will optionally form a layer of the non-fibrous polymeric material adjacent the fibrous matrix.

In some embodiments, the hybrid polymeric structure is formed by the non-fibrous polymeric material and the fibrous matrix over a series of alternating steps. For example, the hybrid polymeric structure may be created incrementally by adding a suitable amount of polymeric liquid, such as liquid silicone, to the surface of a mandrel, or another forming substrate, and electrospinning the plurality of fibers into the liquid polymer. The mixture of polymeric liquid and the fibers are cured, as desired. A second suitable amount of polymeric liquid is optionally added over the partially or fully cured mixture, followed by another electrospinning process that again adds fibers into the polymeric liquid. Repeating these steps yields an iterative process that can be used to build up the hybrid polymeric structure.

In some embodiments, the hybrid polymeric structure includes the polymeric network of a given polymeric material, for example, the first polymeric material. The polymeric network is optionally formed by embedding the first polymeric material in the pores of the fibrous matrix made of another material, for example, the second polymeric material. In some embodiments, the polymer network is formed using various processes, for example, by dip coating, spraying, electro spraying a polymeric material onto the fibrous matrix. Other exemplary processes include, but are not limited to, electrospinining, injection molding and extruding a polymeric material over the fibrous matrix. Combinations of the various processes herein can be used to construct the hybrid polymeric structure, in some embodiments.

In some embodiments, the hybrid polymeric structure includes a cross-linked hydrophilic polymer coating. To form a cross-linked hydrophilic polymer coating, a hydrogel solution is applied to at least a portion of the formed fibrous matrix, as discussed previously herein. For example, in some embodiments, the hydrogel solution may include a range of about 0.1 wt % to 5 wt % PEG in the solution. In some embodiments, the hydrogel solution may include a range of about 0.1 wt % to 1 wt % PEG, about 1.0 wt % to 1.5 wt % PEG, or about 1.0 wt % to 5 wt % PEG in the solution. The hydrogel solution may be applied to the fibrous matrix using various application methods. Examples of possible application methods include, but are not limited to, dip coating, roll coating, spray coating, flow coating, electrostatic spraying, plasma spraying, spin coating, curtain coating and silkscreen coating.

The hydrogel may be subjected to a curing process to crosslink individual hydrogel polymer chains together. The curing process may depend on the curing initiator. In some embodiments, the hydrogel curing process may be initiated by heat or UV light. In other embodiments, vacuum pressure may be used to initiate the free radical initiator and/or to optimize the hydrogel cross-linking process. In some embodiments, the coated fibrous matrix may be placed into an oven to initiate or accelerate the curing of the hydrogel. In other embodiments, the hydrogel curing process may be initiated by UV light.

In some embodiments, the fibrous matrix of the cross-linked hydrophilic polymer coating is subjected to surface treatment prior to, during or after a hydrogel coating application. In some embodiments, the surface treatment is optionally used to change the surface characteristics of the fibrous matrix. The surface treatment may optionally change the surface characteristic of the fibrous matrix to facilitate the hydrogel coating application process. In certain embodiments, the surface treatment may clean the surface, activate the surface, neutralize surface static, and/or realign fiber orientation in the fibrous matrix. One example of surface processing includes, but is not limited to, plasma treating.

Plasma treating is a surface modification process that uses ionized gas molecules to alter the surface characteristics of a polymer. Plasma treatment may remove volatile organic compounds from a polymeric material. Also, plasma treatment may be used to activate the surface of a polymeric material that does not typically bond easily, or exhibits hydrophobic characteristics. In some embodiments, plasma treating may be used to temporarily activate the surface of the fibrous matrix before the hydrogel 346 is applied.

Figure 8:
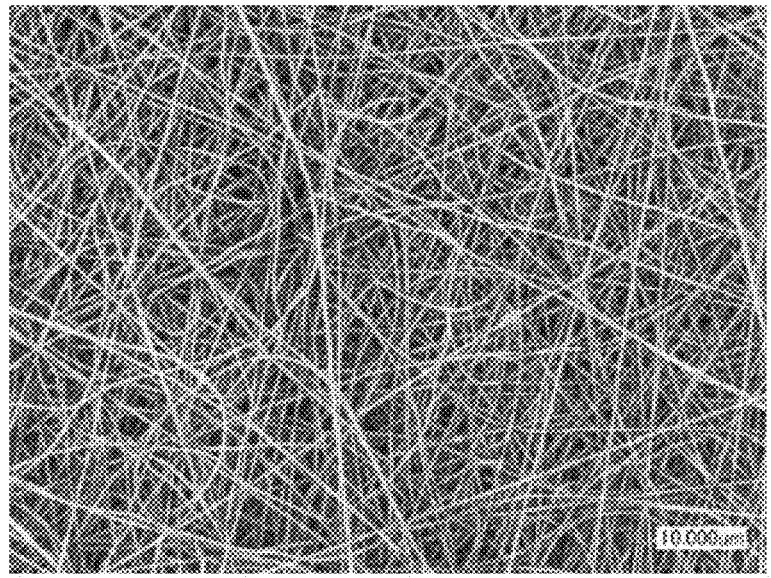
FIG. 8 is a light microscope image of a poly(vinylidene fluoride-co-hexafluoropropene) (PVDF-HFP) fibrous matrix.
Figure 9:
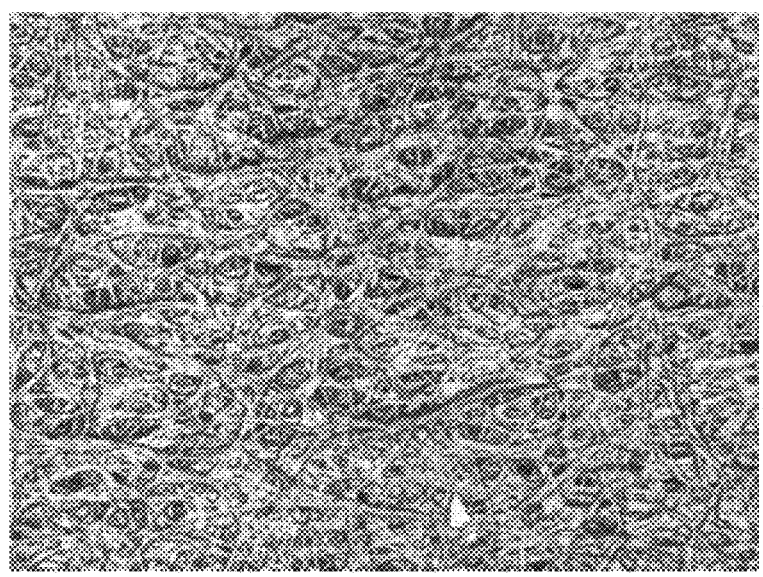
FIG. 9 is a confocal microscope image of a cross-linked hydrophilic polymer coating including a polyethylene glycol (PEG) hydrogel and a PVDF-HFP fibrous matrix.
Figure 10:
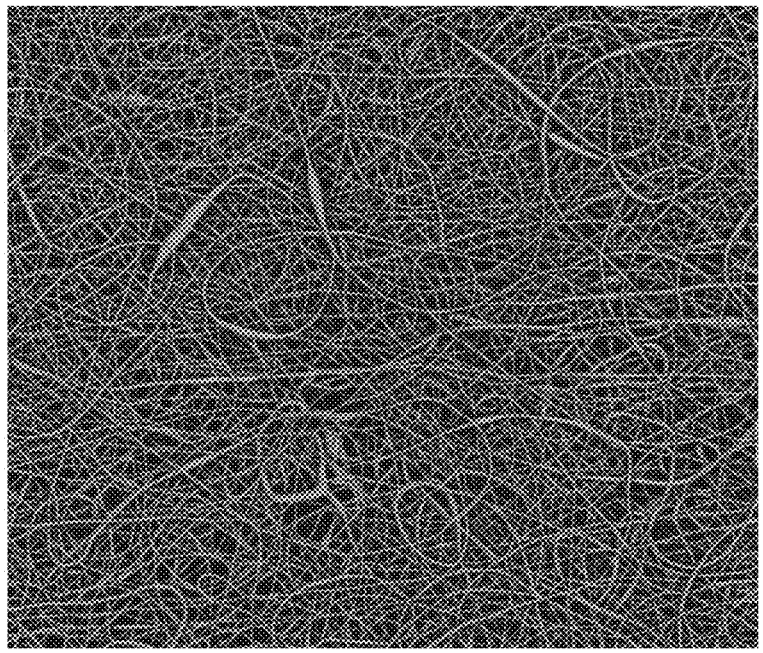
FIGS. 10 and 11 are confocal microscope images of an alternative embodiment of the cross-linked hydrophilic polymer coating including a PEG hydrogel and a PVDF-HFP fibrous matrix shown at 1000× and 2500× magnification, respectively.
Figure 11:
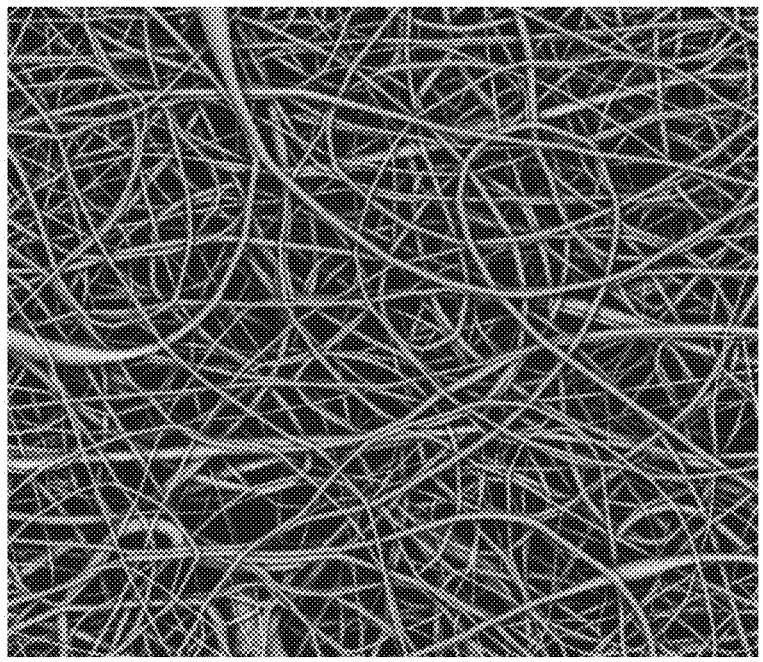

Specific examples of a fibrous matrix and a cross-linked hydrophilic polymer coating are provided herein. FIG. 8 provides an image of a fibrous matrix formed by poly (vinylidene fluoride-co-hexafluoropropene) (PVDF-HFP) fibers. FIGS. 9-11 show images of a cross-linked hydrophilic polymer coating formed by a polyethylene glycol (PEG) hydrogel and a PVDF-HFP fibrous matrix. In some embodiments, the concentration of the hydrogel solution can affect whether the hydrogel becomes disposed in the pores between the fibers and/or over the surface of the fibers after the hydrogel application process. As shown by FIG. 9, the hydrogel is disposed in the spaces, i.e. pores, between the fibers and over the surface of the fibers of the fibrous matrix after applying a higher concentration hydrogel solution, for example, a 10 wt % PEG in an isopropyl alcohol (IPA) solution, to the fibrous matrix. FIGS. 10 and 11 show the PEG hydrogel disposed over the surface of the fibers of the fibrous matrix without being disposed within the pores of the fibrous matrix after applying a lower concentration hydrogel solution, for example, a 1.0 wt % PEG in the IPA solution, to the fibrous matrix.

In some embodiments, heat treatments are applied to the hybrid polymeric structure or a precursor of the hybrid polymeric structure, for example, the fibrous matrix, embedded fibrous matrix, cross-linked hydrophilic polymer coating, non-fibrous polymeric layer and/or combinations thereof. In some embodiments, the heat treatment is optionally used to change the material characteristics of entire fibrous matrix. A non-limiting example includes using heat treatment to help create and/or strengthen the fiber-to-fiber bonds within the fibrous matrix. Another non-limiting example includes using heat treatment to help create and/or strengthen the bonds between the hydrogel molecules within the cross-linked hydrophilic coating. In some embodiments, the hybrid polymeric structure or precursors of the hybrid polymeric structure may undergo heat treatment prior to or subsequent to adding another polymeric material. Exemplary heat treatments include, but are not limited to, sintering.

Sintering is a heat treatment process that can be used to fuse together polymeric materials. In some embodiments, a targeted polymeric material is exposed to a temperature near or at its glass temperature. In some embodiments, the hybrid polymeric structure is subjected to a temperature near or at the glass temperature of at least one of its precursor materials. In some embodiments, the hybrid polymeric structure is sintered to help improve the bond strength of the fiber-to-fiber bonds within the fibrous matrix. In some embodiments, the hybrid polymeric structure is sintered to help improve the bond strength between the hydrogel molecules within the cross-linked hydrophilic coating. In a non-limiting example, the hybrid polymeric structure, composed of the fibrous matrix of the first polymeric material and the embedded polymer of the second polymeric material, sintered by subjected the structure to the glass transition temperature of the fibrous matrix. Consequently, in some embodiments, the fibers of the fibrous matrix become fused together when subjected to the sintering process, helping to create a more robust, durable hybrid polymeric structure.

Figure 12:
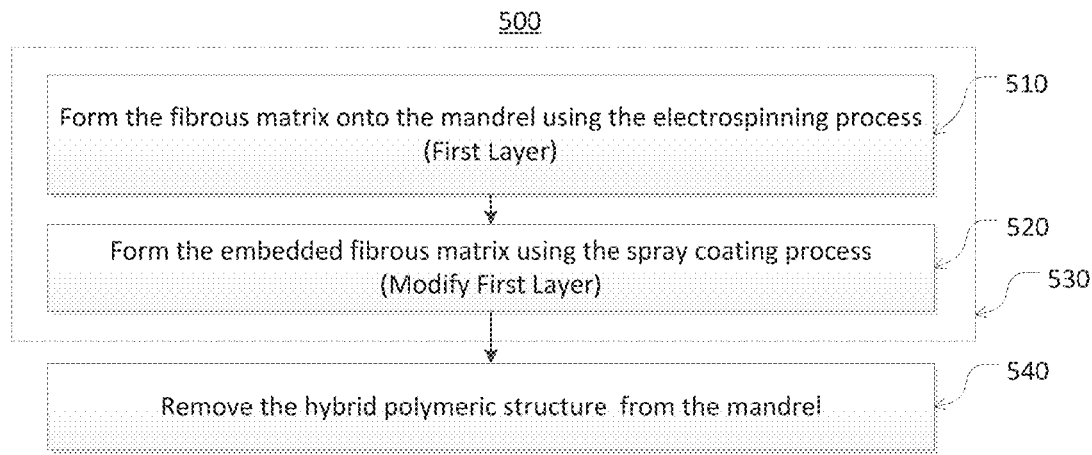
FIGS. 12-14 are various embodiments of a method for manufacturing the tubular medical device of FIG. 2, according to embodiments of the present invention.
Figure 13:
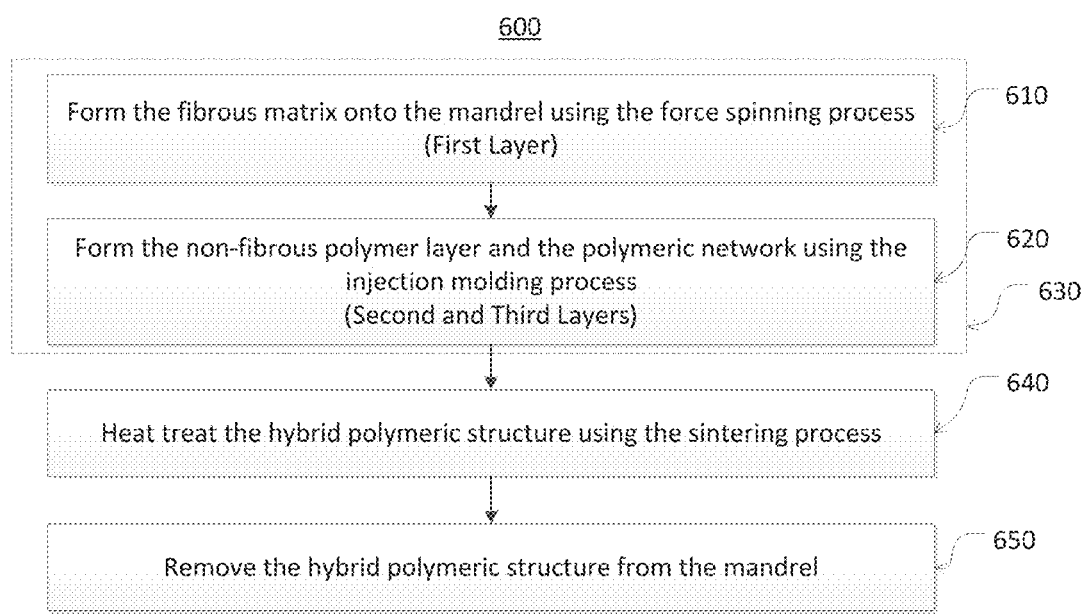
Figure 14:
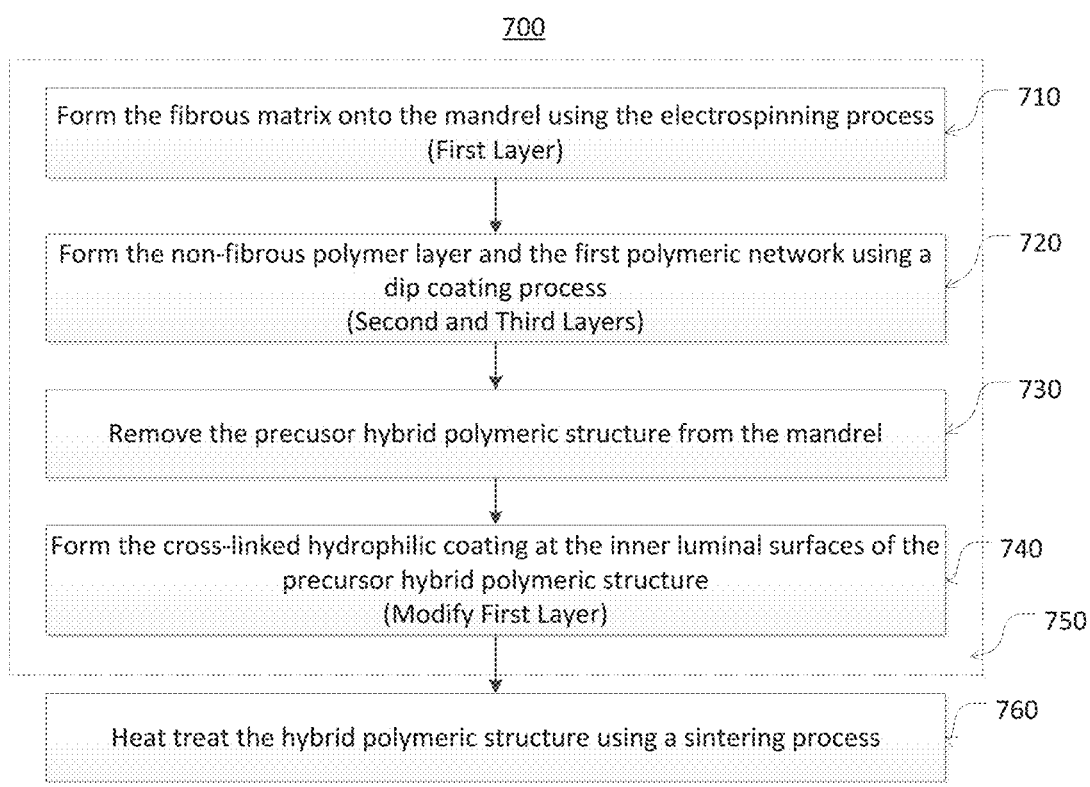

FIGS. 12-14 are flow charts illustrating a method 500-700 of manufacturing the hybrid polymeric structure. The present invention is more particularly described in the following non-limiting examples, which is intended as illustration only, since numerous modifications and variations within the scope of the present invention have been discussed previously herein and/or will be apparent to those skilled in the art.

The method 500-700 may be used to form the hybrid polymeric structure of various tubular medical devices including, for example, an implantable cardiac pacing lead or a tracheostomy tube. In some embodiments, the method 500-700 yields suitable physical properties for a given medical application.

The method 500 includes creating some embodiments of the hybrid polymeric structure having one layer composed of an embedded fibrous matrix made of two chemically and/or physically distinct polymeric materials. In some embodiments, the first layer includes the fibrous matrix of a suitable thickness that is formed on the mandrel using the electrospinning process (block 510). In some embodiments, the fibrous matrix is composed of the first polymeric material.

In some embodiments, the fibrous matrix first layer is modified such that the first layer becomes an embedded fibrous matrix. The embedded fibrous matrix is formed by spray coating the polymeric network made of the second polymeric material into the fibrous matrix (block 520), in some embodiments. The second polymeric material becomes the embedded polymer within the fibrous matrix when the spray coating process delivers a given amount of the second polymeric material that does not exceed the pore saturation point of the fibrous matrix, in some embodiments.

The fibrous matrix of the first polymeric material and the embedded polymer of the second polymeric material together create the hybrid polymeric structure (block 530), in some embodiments.

The hybrid polymeric structure is removed from the mandrel to yield a structure having a tubular body (block 540), in some embodiments.

The method 600 includes creating some embodiments of the hybrid polymeric structure having three layers: the first layer (e.g. inner layer) comprising the fibrous matrix, the second layer (e.g. intermediate layer) comprising the embedded fibrous matrix, and the third layer (e.g. outer layer) comprising the non-fibrous polymeric layer. Furthermore, in some embodiments, the hybrid polymeric structure includes three layers composed of at least two chemically and/or physically distinct polymeric materials: the first layer is composed of the first polymeric material, the second layer is composed of the first and second polymeric materials, and the third layer is composed of the second polymeric material.

In some embodiments, the fibrous matrix is formed on the mandrel using a force spinning process (block 610). The fibrous matrix is composed of the first polymeric material and creates the first layer of the hybrid polymeric structure.

In some embodiments, the second layer is made of the polymeric network and the third layer is made of the non-fibrous polymeric layer. The non-fibrous polymeric layer and the polymeric network, both made of the second polymeric material, are formed using the injection molding process (block 620), according to embodiments of the present invention. The second layer includes portions of the fibrous matrix that are embedded with the second polymeric material, i.e. the embedded polymer matrix, in some embodiments. The second layer is formed when the second polymeric material is injected onto the outer surface of the fibrous matrix and embeds into at least a portion of the pores of the fibrous matrix, as desired. In some embodiments, the injection molding process injects a given amount of the second polymeric material that exceeds the pore saturation point of the fibrous matrix. As such, the third layer includes the non-fibrous polymeric layer formed by the second polymeric material that is optionally disposed over the outer surface of the fibrous matrix.

The fibrous matrix of the first polymeric material, the polymeric network of the second polymeric material, and the non-fibrous polymeric layer of the second polymeric material together create a hybrid polymeric structure (block 630).

In some embodiments, the hybrid polymeric structure is sintered to help improve the bond strength of the fiber-to-fiber bonds within the fibrous matrix (block 640).

The hybrid polymeric structure is removed from the mandrel to yield a tubular shaped medical component or device (block 650), as desired. In some embodiments, the hybrid polymeric structure can be removed from the mandrel earlier in the process, for example, prior to sintering the hybrid polymeric structure (block 640).

The method 700 includes creating an embodiment of a hybrid polymeric having three layers: the first layer (e.g. inner layer) composed of the cross-linked hydrophilic coating, the second layer (e.g. intermediate layer) composed primarily of the embedded fibrous matrix having two different polymeric networks, and the third layer (e.g. outer layer) composed primarily of the non-fibrous polymeric layer. Furthermore, in some embodiments, the hybrid polymeric structure includes three layers composed of at least three chemically and/or physically distinct polymeric materials: the first layer is composed of the first and third polymeric materials; the second layer is composed of the first, second and third polymeric materials; and the third layer is composed of the second polymeric material.

The fibrous matrix can be formed on the mandrel using the electrospinning process (block 710). In some embodiments, the fibrous matrix is composed of the first polymeric material and creates the first layer of the hybrid polymeric structure.

The non-fibrous polymeric layer and the first polymeric network, both made of the second polymeric material, can be formed using the dip coating process (block 720), according to embodiments of the present invention. The second polymeric material may be applied onto the outer surface of the fibrous matrix and embedded into at least a portion of the pores of the fibrous matrix, in some embodiments. The second layer is formed by the portions of the fibrous matrix that have become embedded with the second polymeric material, i.e. the embedded polymer matrix, in some embodiments.

In some embodiments, the dip coating process applies a suitable amount of the second polymeric material that exceeds the pore saturation point of the fibrous matrix. As such, the second polymeric material can be disposed over the outer surface of the fibrous matrix to form the non-fibrous polymeric layer, e.g. the third layer.

In this exemplary method, the fibrous matrix of the first polymeric material, the non-fibrous polymeric layer of the second polymeric material and the first polymeric network of the second polymeric material together create a precursor hybrid polymeric structure. The precursor hybrid polymeric structure can be removed from the mandrel for further processing (block 730). In some embodiments, the precursor hybrid polymeric structure can be removed from the mandrel earlier or later in the process.

In some embodiments, the hybrid polymeric structure may include the cross-linked hydrophilic coating. The cross-linked hydrophilic coating can be formed by modifying the first layer. In some embodiments, the hydrogel made of the third polymeric material is applied to the fibrous matrix of the tubular precursor device at the inner luminal surfaces using the dip coating process. In some embodiments, the hydrogel is disposed within a portion of the accessible pores at the inner luminal surface, creating the second polymeric network. In some embodiments, a layer of the hydrogel may cover the exterior surface of the fibrous matrix at the inner luminal surface of the tubular body. The hydrogel and the fibrous matrix can be subsequently heat cured to form the cross-linked hydrophilic coating (block 740).

As shown in method 700, the cross-linked hydrophilic coating can be formed in at least a portion of the fibrous (block 740) after a precursor hybrid structure has been created from the first and second polymeric materials (block 720), according to some embodiments. Alternatively, in other embodiments, the second polymeric material can be added to the first polymeric material, e.g. fibrous matrix, to form the hybrid structure (block 720) after the cross-linked hydrophilic coating has been formed in at least a portion of the fibrous matrix (block 740). This is possible because the hydrogel solution can be applied to the fibrous matrix to form the cross-linked hydrophilic coating either before or after the first polymeric material, e.g. fibrous matrix, has combined with the second polymeric material to form the hybrid structure.

The non-fibrous polymeric layer of the second polymeric, the first polymeric network of the second polymeric material, and the cross-linked hydrophilic coating comprising the fibrous matrix made from the first polymeric material and the second polymeric network of the third polymeric material, together create the hybrid polymeric structure (block 750), in some embodiments.

The hybrid polymeric structure can be sintered to help improve the bond strength of the fiber-to-fiber bonds within the fibrous matrix (block 760). In some embodiments, the hybrid polymeric structure is sintered to help improve the bond strength between the hydrogel molecules within the cross-linked hydrophilic coating.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

Example 1

The present invention is more particularly described in the following example, which is intended as illustration only, since numerous modifications and variations within the scope of the present invention will be apparent to those skilled in the art.

Drag Force Comparison Study

Control Samples

The control sample ("Sample A") was a commercially available tracheostomy tube (manufactured by Bivona) having an inner diameter (I.D.) of about 9.5 mm and an outer diameter (O.D.) of about 11.2 mm.

Test Samples

One test sample ("Sample B") was formed of PTFE tubing with an I.D of about 9.5 mm and an outer diameter (O.D.) of about 11.2 mm.

Two test samples ("Sample C" and "Sample D") were constructed of a hybrid polymeric structure that included an outer layer made of silicone and an inner layer made of a cross-linked hydrophilic polymer coating.

The inner tubular layers of Samples C and D were constructed with a hybrid polymeric structure that included a non-fibrous polymeric layer made of silicone and a cross-linked hydrophilic polymer coating comprising a PVDF-HFP fibrous matrix and a PEG hydrogel polymeric network. The hybrid polymeric structure and the cross-linked hydrophilic polymer coating may be constructed using the processes and methods previously discussed herein.

Samples C and D were constructed with an I.D of about 9.5 mm and an outer diameter (O.D.) of about 11.2 mm. The cylindrical inner layer tubes of Samples C and D were constructed by forming fibers onto a mandrel with a suitable diameter to produce tubes with the I.D. of 9.5 mm. Samples C and D were removed from the mandrel prior to testing.

Drag Force Test Method

Test and control samples were each labeled accordingly and placed into a test fixture having a tortuous path, or curvature, simulating an exemplary anatomical trachea airway.

A bronchoscope having a 6.8 mm outer diameter was placed into the lumen of each sample. The proximal end of the bronchoscope was attached to a materials testing machine, e.g. Instron Tester.

The bronchoscope was advanced and retracted a distance of 2 inches within each test sample along the tortuous path. The maximum force measurement was recorded for each sample while the bronchoscope was advanced and retracted within each sample.

Results

TABLE 1

Drag force data

| Sample | Max. Force lbf. |
|---|---|
| A | 4.24 |
| B | 0.33 |
| C | 0.91 |
| D | 1.04 |

The maximum force data for the test samples and the control sample are shown in Table 1. The maximum force value measures frictional resistance between the outer surface of the bronchoscope and the inner surface of the test samples while the bronchoscope is moving within the lumen of each test sample. As such, the maximum force value provides an indication of the lubricity characteristic of the inner lumen of each sample.

Table 1 shows that the commercial available tracheostomy tube (Sample A) had the highest maximum force while the PTFE tube (Sample B) had the lowest maximum force. The average maximum force of the tube samples made of the hybrid polymeric structure (Samples C and D) was 0.975 lbf. The average max. force of the hybrid polymeric structured tubes (Samples C and D) was significantly lower than the commercial available tracheostomy tube (Sample A), but slightly higher than the PTFE tube (Sample B).

The results show that test samples made of the hybrid polymeric structure (Samples C and D) have lubricous inner lumens that produce substantially less frictional resistance to movement of a bronchoscope when compared to the currently commercial available tracheostomy tube (Sample A).

We claim:

1. A medical device made of a hybrid polymeric structure comprising:
   a tubular body including a first layer and a second layer;
   the first layer including a fibrous matrix comprising a plurality of randomly oriented nanofibers made at least in part of a first polymeric material and pores formed between at least a portion of the nanofibers; and
   the second layer made at least in part of a second polymeric material;
   wherein at least a portion of the second layer made of the second polymeric material is disposed about and between the plurality of nanofibers such that at least a portion of the second polymeric material is embedded into at least a portion of the pores of the fibrous matrix;
   wherein the first layer further comprises a cross-linked hydrogel made at least in part of a third polymeric material disposed about and between the plurality of nanofibers.

2. The medical device of claim 1, wherein the first layer includes the fibrous matrix made at least in part of the first polymeric material comprising poly(vinylidene fluoride-co-hexafluoropropylene) (PVDF HFP).

3. The medical device of claim 1, wherein the fibrous matrix comprising the plurality of randomly oriented nanofibers, wherein a portion of the nanofibers are fused to one another.

4. The medical device of claim 1, wherein the second layer is made at least in part of the second polymeric material comprising silicone.

5. The medical device of claim 1, wherein the cross-linked hydrogel is made at least in part of the third polymeric material comprising polyethylene glycol (PEG).

6. The medical device of claim 1, further including a third layer disposed between the first layer and the second layer, the third layer including a portion of the fibrous matrix and not including the second polymeric material or the third polymeric material.

7. The medical device of claim 1, wherein the first layer forms a first surface of the device and the second layer forms a second surface of the device.

8. The medical device of claim 7, wherein the first surface is an inner surface of the tubular body and the second surface is an outer surface of the tubular body.

9. A medical device comprising:
   a tubular body including an outer surface, an inner surface, and a layer extending from the first surface to the second surface, the layer including:
   a fibrous matrix including a plurality of randomly oriented nanofibers made at least in part of a first polymeric material and pores formed between at least a portion of the nanofibers;
   a first polymeric network disposed within at least a portion of the pores, the first polymeric network made at least in part of a second polymeric material, the second polymeric material different from the first polymeric material; and
   a second polymeric network disposed within at least a portion of the pores, the second polymeric network made a least in part of a third polymeric material, the third polymeric material different from the first polymeric material and the second polymeric material.

10. The medical device of claim 9, wherein the first polymeric material includes poly(vinylidene fluoride-co-hexafluoropropylene).

11. The medical device of claim 9, wherein the second polymeric material includes silicone.

12. The medical device of claim 9, wherein the first polymeric material is hydrophobic and the third polymeric material is hydrophilic.

13. A medical device comprising:
a tubular body including an outer surface, an inner surface, and a layer extending from the outer surface to the inner surface, the layer including:
a fibrous matrix including a plurality of randomly oriented nanofibers, the plurality of randomly oriented nanofibers including:
a first plurality of nanofibers made at least in part of a first polymeric material, wherein the first polymeric material includes poly(styrene-isobutylene-styrene), polyisobutylene polyurethane, or a combination thereof; and
a second plurality of nanofibers made a least in part of a second polymeric material, wherein the sec ond polymeric material includes polyethylene glycol.

14. The medical device of claim 13, wherein the first plurality of nanofibers consists of the first polymeric material; and the second plurality of nanofibers consists of the second polymeric material.

15. The medical device of claim 13, wherein the first polymeric material is hydrophobic and the second polymeric material is hydrophilic.

16. The medical device of claim 13, wherein the first polymeric material is a thermoset material and the second polymeric material is a thermoplastic material, or the second polymeric material is a thermoset material and the first polymeric material is a thermoplastic material.

17. The medical device of claim 13, wherein the first polymeric material is an electrically conductive material and the second polymeric material is an electrically non-conductive material, or the second polymeric material is an electrically conductive material and the first polymeric material is an electrically non-conductive material.

18. The medical device of claim 13, wherein the first polymeric material includes poly(vinylidene fluoride-co-hexafluoropropylene).

* * * * *